US012515301B2

(12) United States Patent
Lang et al.

(10) Patent No.: US 12,515,301 B2
(45) Date of Patent: Jan. 6, 2026

(54) SET SCREW DRIVER

(71) Applicant: K2M, Inc., Leesburg, VA (US)

(72) Inventors: Brittany Lang, Warrenton, VA (US); Michael Barrus, Redondo Beach, CA (US)

(73) Assignee: VB Spine US Opco LLC, Leesburg, VA (US)

( * ) Notice: Subject to any disclaimer, the term of this patent is extended or adjusted under 35 U.S.C. 154(b) by 215 days.

(21) Appl. No.: 17/896,319

(22) Filed: Aug. 26, 2022

(65) Prior Publication Data

US 2023/0074244 A1 Mar. 9, 2023

Related U.S. Application Data

(60) Provisional application No. 63/240,595, filed on Sep. 3, 2021.

(51) Int. Cl.
*B25B 23/10* (2006.01)
*A61B 17/70* (2006.01)

(52) U.S. Cl.
CPC ........ *B25B 23/105* (2013.01); *A61B 17/7091* (2013.01)

(58) Field of Classification Search
CPC .. B25B 23/105; B25B 23/101; A61B 17/7091
USPC .................................. 81/452, 436, 444, 448
See application file for complete search history.

(56) References Cited

U.S. PATENT DOCUMENTS 192,423 A 6/1877 Elterich
1,131,990 A * 3/1915 Bocorselski ............ B23B 31/12 279/36
1,359,384 A * 11/1920 Watt ...................... B25B 23/106 81/448
1,433,163 A * 10/1922 Alexander ............. B25G 1/007 81/177.85
3,288,184 A 11/1966 Kyser
4,060,114 A * 11/1977 Matsushima ......... B25B 15/008 81/460
4,553,455 A 11/1985 Wilcox et al.
5,667,513 A 9/1997 Torrie et al.
6,206,696 B1 3/2001 Day
6,394,806 B1 5/2002 Kumar
7,137,322 B2 11/2006 Mark et al.
7,314,374 B2 1/2008 Augthun et al.
7,452,361 B2 11/2008 Kreidler
8,262,670 B2 9/2012 Laubert et al.
8,343,165 B2 1/2013 Berrevoets
8,347,768 B2 1/2013 Witte
(Continued)

*Primary Examiner* — Hadi Shakeri
(74) *Attorney, Agent, or Firm* — Lerner David LLP

(57) ABSTRACT

A tool for use with a fastener includes a drive shaft extending along a longitudinal axis from a proximal end to a distal end. The tool includes an engaging tip extending from the distal end, the engaging tip sized and shaped to detachably engage a receiving portion of the fastener, wherein the engaging tip is rotationally fixed to the fastener when the engaging tip is engaged with the fastener. The tool includes a compressible winged member extending distally from the drive shaft, the compressible winged member moveable between compressed and uncompressed positions. In the uncompressed position, the compressible winged member spans a distance greater than an internal diameter of a portion of the receiving portion.

15 Claims, 8 Drawing Sheets

(56) References Cited

U.S. PATENT DOCUMENTS

| | | | | |
|---|---|---|---|---|
| 9,032,847 | B2 * | 5/2015 | Duitsman | B25B 23/0007<br>81/438 |
| 9,067,307 | B2 | 6/2015 | Kozak | |
| 9,375,830 | B2 | 6/2016 | Kana et al. | |
| 10,343,267 | B2 * | 7/2019 | Sanders | B25B 15/001 |
| 10,646,981 | B2 * | 5/2020 | Kennedy | B25B 23/108 |
| 10,874,448 | B2 | 12/2020 | Rees et al. | |
| 2003/0233095 | A1 | 12/2003 | Urbanski et al. | |
| 2005/0033307 | A1 | 2/2005 | Cook et al. | |
| 2008/0269768 | A1 | 10/2008 | Schwager et al. | |
| 2008/0275459 | A1 * | 11/2008 | Dickinson | B25B 23/105<br>606/104 |

* cited by examiner

SET SCREW DRIVER

CROSS-REFERENCE TO RELATED APPLICATIONS

The present application claims the benefit of the filing date of U.S. Provisional Patent Application No. 63/240,595 filed Sep. 3, 2021, the disclosure of which is hereby incorporated by reference in its entirety.

BACKGROUND OF THE INVENTION

Fastener-driving tools come in various shapes and sizes for mating with fasteners. A firm, stable grip is strongly desired between the tool and the fastener so that the tool can be rotatably fixed to the receiving portion of the fastener (e.g., a screwhead) to smoothly actuate the fastener. Anything less than a strong engagement may result in the inability to provide enough torque to fully actuate the fastener and any relative rotation between the tool and the fastener (e.g., slippage) may lead to deformation of the fastener and eventually an inability to actuate the fastener. As such, different shapes and structures have been developed to improve the engagement between such tools and fasteners.

In the context of surgical procedures, another problem that often arises is the inability to hold the fastener in engagement with the tool. Such procedures are often performed in limited spaces that don't permit for the separate holding of the fastener in engagement with the tool, as would be done in, for instance, a carpentry setting. Indeed, it is often beneficial to provide a driver that includes structure to self-retain the fastener thereto.

Particularly in the surgical context, current drivers may be used with set screws that have a consistent bore cut all the way through. The use of such set screws and corresponding drivers creates significant risk of manipulating the set screw in an improper orientation, e.g., inserting the driver into the wrong end of the set screw. Further, secure engagement between the driver and the set screw is a critical aspect of any procedure and thus can be desirably improved upon for increased effectiveness and efficiency.

BRIEF SUMMARY OF THE INVENTION

The present disclosure describes a tool that can be used to engage and actuate a fastener. In some examples, the tool is a set screw retaining driver that is configured to securely engage and actuate a set screw during the implantation of pedicle screws and a spinal rod in a patient. The tool includes an engaging tip having a corrugated portion shaped to engage a proximal receiving portion of the set screw, and a distal head shaped to engage a distal receiving portion of the set screw. The tool further includes a compressible winged member which is biased to extend radially outward from the distal head in a resting state, and configured to be compressed radially inward when the distal head is engaged with the corresponding receiving portion of the set screw. The spring bias of the compressible winged member creates an interference fit between the compressible winged member and the set screw and strongly secures the engagement between the driver and the set screw.

In one aspect of the disclosure, a tool for use with a fastener may include a drive shaft extending along a longitudinal axis from a proximal end to a distal end, an engaging tip extending from the distal end, the engaging tip sized and shaped to detachably engage a receiving portion of the fastener, wherein the engaging tip is rotationally fixed to the fastener when the engaging tip is engaged with the fastener, and a compressible winged member extending distally from a cavity defined by the drive shaft. The compressible winged member may be moveable between compressed and uncompressed positions. In the uncompressed position, the compressible winged member may have a width greater than a portion of the receiving portion. In the compressed position, the compressible winged member may have a width less than the receiving portion. The drive shaft may have a distal portion adjacent the engaging tip, and the distal portion may define a cavity extending along the longitudinal axis for receiving a portion of the engaging tip and/or the compressible winged member. The compressible winged member may include a first wing and a second wing connected by a connecting base. A distal end of the compressible winged member may be configured to be compressed.

The engaging tip may include includes a proximal stem positioned within the drive shaft, the proximal stem defining at least a portion of a slot adapted to receive the compressible winged member. The engaging tip may include a circular base coupled to a distal end of the proximal stem, the circular base defining at least a portion of the slot adapted to receive the compressible winged member. The engaging tip may include a corrugated portion extending distally from the circular base, the corrugated portion defining a plurality of ridges and grooves between each adjacent pair of ridges. The corrugated portion may define at least a portion of the slot adapted to receive the compressible winged member. The engaging tip may include a distal head extending distally from the corrugated portion and defining a circumference, the distal head defining at least a portion of the slot adapted to receive the compressible winged member. The compressible winged member may include a first wing protruding radially beyond the circumference of the distal head when in a resting configuration, defining a first gap between the first compressible wing and a center portion of the distal head. The first wing may be biased in the uncompressed position and configured to be compressed radially inward to close the first gap and have an outer edge of the first wing align with the circumference of the distal head when in the compressed position. The compressible winged member may include a second wing protruding radially beyond the circumference of the distal head when in the uncompressed position, defining a second gap between the second wing and the center portion of the distal head. The second wing may be biased in the uncompressed position and configured to be compressed radially inward to close the second gap and have an outer edge of the second wing align with the circumference of the head when in a compressed position.

The first wing and the second wing may be positioned opposite each other along the circumference of the distal head. Each of the first and second wings may define a beveled surface on a distal radially outer edge of the first and second wings, each beveled surface adapted to contact an internal edge of the fastener. The compressible winged member may be disposed within a slot of the engaging tip. The compressible winged member may include a first wing disposed within a first slot of the engaging tip and a second wing disposed within a second slot of the engaging tip. The compressible winged member may be non-unitary with the drive shaft and the engaging tip.

According to another aspect of the disclosure, a method of using a tool for use with a fastener may include inserting an engaging tip and a compressible winged member of the tool into a receiving portion of the fastener and contacting a distal surface of the compressible winged member to an internal ledge of the fastener to compress the compressible winged member radially inward within the receiving portion; and rotating the tool to rotate the fastener. The method may further include removing the compressible winged member and the engaging tip of the tool from the fastener by applying a force to the tool in a proximal direction relative to the fastener. The force applied may be greater than a frictional force between the compressible winged member and the fastener. The method may further include removing the compressible winged member and the engaging tip of the tool from the fastener by applying a force to the fastener in a distal direction relative to the tool. The inserting step may include pressing a first distal beveled surface of a first wing and a second distal beveled surface of a second wing against the fastener.

According to another aspect of the disclosure, a system for inserting a fastener may include a set screw comprising a body having an external threading and defining an internal bore, the bore having a first proximal portion having a first diameter and a second distal portion having a second diameter smaller than the first diameter. The system may further include a tool comprising a drive shaft extending along a longitudinal axis from a proximal end to a distal end, the drive shaft defining a cavity at the distal end, an engaging tip extending distally from the drive shaft for engaging with the set screw, and a compressible winged member may extend distally from the drive shaft for engaging with the set screw.

The internal bore of the set screw may include a first proximal receiving portion having a first diameter and a second distal receiving portion having a second diameter smaller than the first diameter. The engaging tip of the tool may include a corrugated portion and the first proximal receiving portion of the internal bore of the set screw may be correspondingly shaped to receive the corrugated portion to rotatably fix the set screw to the tool. The second distal receiving portion having the smaller diameter relative to the first proximal receiving portion may form an interior edge within the set screw bore. The engaging tip may include a distal head having a circumference and the compressible winged member may include a wing protruding radially beyond the circumference of the distal head in an uncompressed position. The wing may be adapted to transition from the uncompressed position to a compressed position when a distal surface of the compressible wing abuts the interior edge of the set screw bore and a pressure is applied between the wing and the interior edge. The second distal receiving portion of the bore of the set screw may be sized and shaped to receive the distal head of the engaging tip and the compressible winged member in the compressed position. The compressible winged member may be biased in the uncompressed position and configured to apply a radially outward force against an interior surface of the set screw bore to form a friction fit engagement.

DETAILED DESCRIPTION

As used herein, the term "proximal," when used in connection with a device, or components of a device, refers to the end of the device closer to the user when the device is being used as intended. On the other hand, the term "distal," when used in connection with a device, or components of a device, refers to the end of the device farther away from the user when the device is being used as intended. As used herein, the terms "about," "generally," "approximately," and "substantially" are intended to mean that slight deviations from absolute are included within the scope of the term so modified.

The device described in the present disclosure is referred to and may be used as a set screw retaining driver. However, it should be understood that the disclosed device is not limited to use with set screws, and may be used for forming a detachable engagement with any object in a rotatably fixed manner, typically for the purpose of actuating (e.g., rotating) the object. For example, the tool may be used with any fastener, such as a bone, wood or metal screw.

Figure 1:
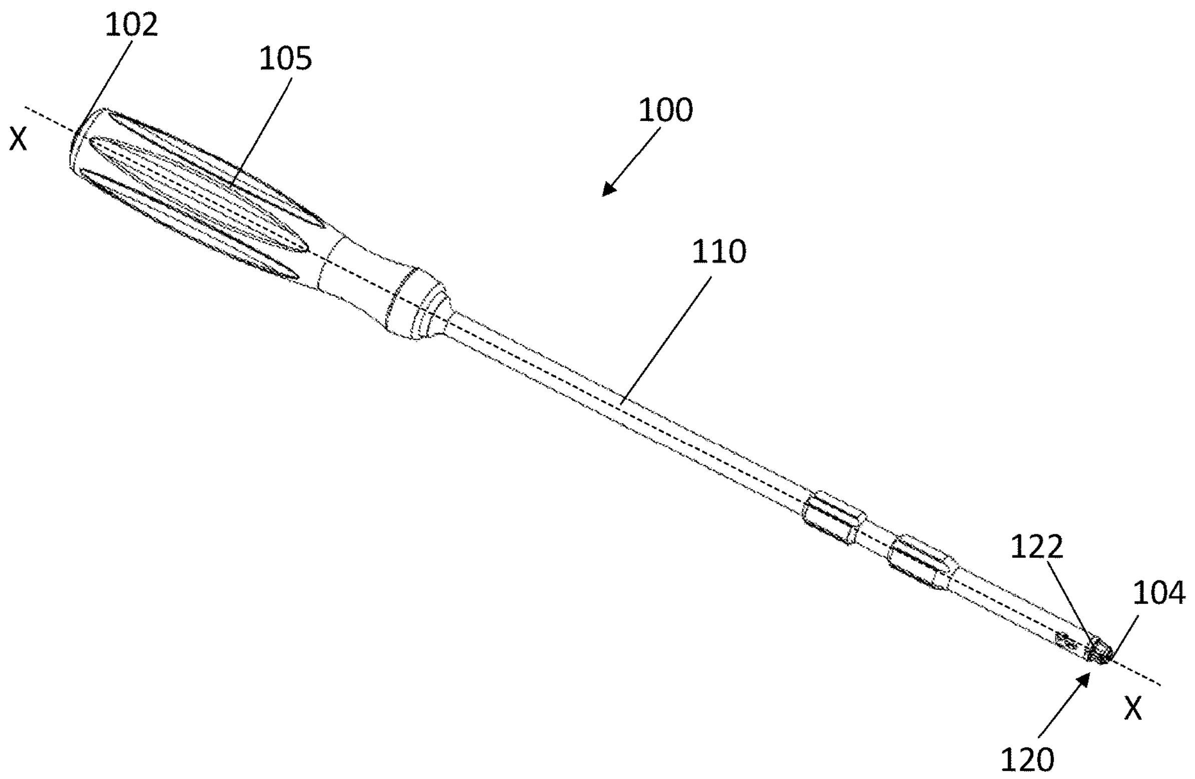
FIG. 1 is a perspective view of a retaining driver according to an embodiment of the disclosure.

FIG. 1 illustrates a retaining driver 100 according to an embodiment of the disclosure. Retaining driver 100 is elongate, extending from a proximal end 102 to a distal end 104 along a longitudinal axis X. Proximal end 102 and portions of the driver 100 near the proximal end 102, such as handle 105, are intended to be grasped and wielded by an operator, such as a surgeon. Such proximal portions may also be engageable with a secondary tool, such as a powered handpiece, robot arm or the like.

Figure 2:
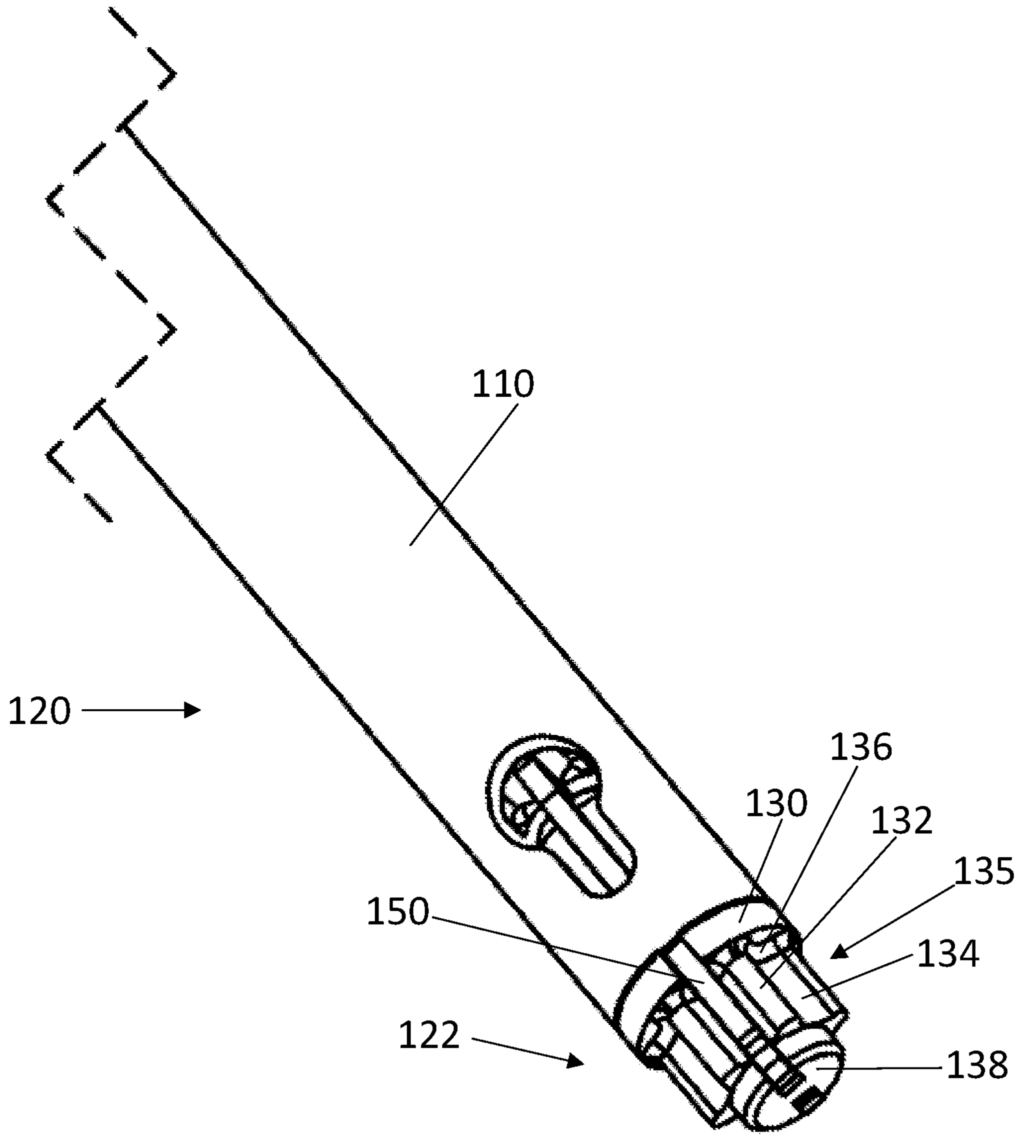
FIGS. 2 and 3 are perspective close-up views of a distal portion of the retaining driver of FIG. 1.
Figure 3:
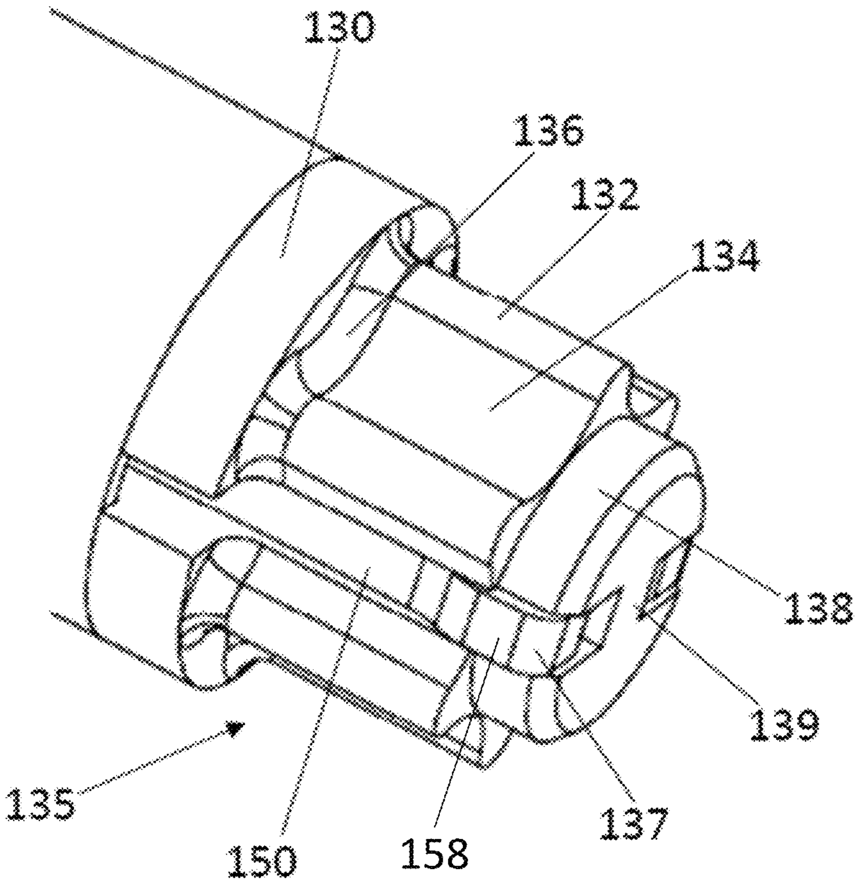

Retaining driver 100 includes a drive shaft 110 extending along axis X, an engaging tip 122 disposed within and extending distally from the drive shaft 110, and a compressible winged member 150 extending along a length of engaging tip 122 and coupled to the drive shaft 110. FIGS. 2 and 3 illustrate close-up views of a distal portion 120 of retaining driver 100, showing drive shaft 110, engaging tip 122, and compressible winged member 150 in an assembled configuration. Engaging tip 122 includes a proximal stem 123 (shown more clearly in FIG. 5) extending within a cavity of a distal portion of drive shaft 110. Engaging tip 122 further extends distally from drive shaft 110, and has a circular base 130 generally aligned with drive shaft 110 (e.g., having a diameter approximately the same as a diameter of the drive shaft) and a generally corrugated portion (or hexalobe) 135 extending distally from circular base 130. In some examples, engaging tip 122 may be coupled to drive shaft 110 by welding a distal end of drive shaft 110 to circular base 130. Corrugated portion 135 includes a plurality of ridges 132 spaced evenly apart along a circumference of corrugated portion 135 of engaging tip 122, each ridge 132 protruding radially and extending in a direction parallel to longitudinal axis X. Each pair of adjacent ridges 132 is separated by an elongate rounded groove 134, and each elongate rounded groove 134 has a proximal rounded groove 136 in communication with and located proximally relative to the elongate rounded groove 134. Extending distally from corrugated portion 135 is a distal head 138 sized and shaped to receive a portion of a compressible winged member 150, which is positioned radially outward of engaging tip 122, radially inward of drive shaft 110, and extends in the proximal-distal direction parallel to longitudinal axis X. It should be understood that engaging tip 122 is not continuous around its circumference, in that proximal stem 123, circular base 130, corrugated portion 135 and distal head 138 each have a circumference that is interrupted defining aligned recesses sized and shaped to receive compressible winged member 150, as discussed further below.

Engaging tip 122 is sized and shaped to mate with a set screw having corresponding female mating portions that are sized and shaped for receiving portions of the engaging tip. It is contemplated that drive shaft 110 and engaging tip 122 may be produced in any size for mating with various sizes of set screws. It is further contemplated that for the purpose of this disclosure, engaging tip 122 is not limited to the precise shape described and illustrated. The illustrated engaging tip 122 includes corrugated portion 135 having a hexalobe shape with six ridges 132 and six elongate grooves 134, however, the engaging tip may have any number of ridges and grooves, or may not be corrugated, so long as it achieves the ability to be rotationally fixed to a fastener. For example, corrugated portion 135 may have only two protruding ridges positioned 180 degrees apart, resembling the shape of a flat-head screwdriver, or four protruding ridges spaced 90 degrees apart resembling the shape of a Phillips-head screwdriver. Further, the ridges may have a flat or sharp peak along the radially outermost surface, rather than the rounded peak as illustrated. The general purpose of corrugated portion 135 is to form a first connection with the set screw such that the driver 100 can be rotatably fixed to the set screw, and may have any shape that will suitably form the desired connection.

Figure 4:
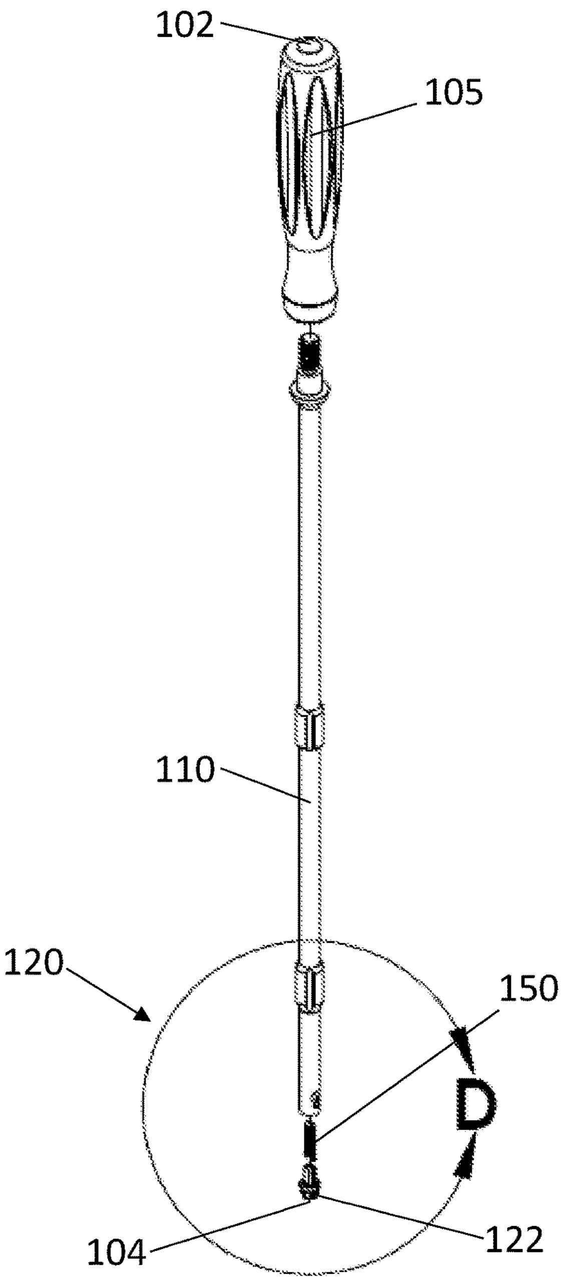
FIG. 4 is an exploded view of the retaining driver of FIG. 1.
Figure 5:
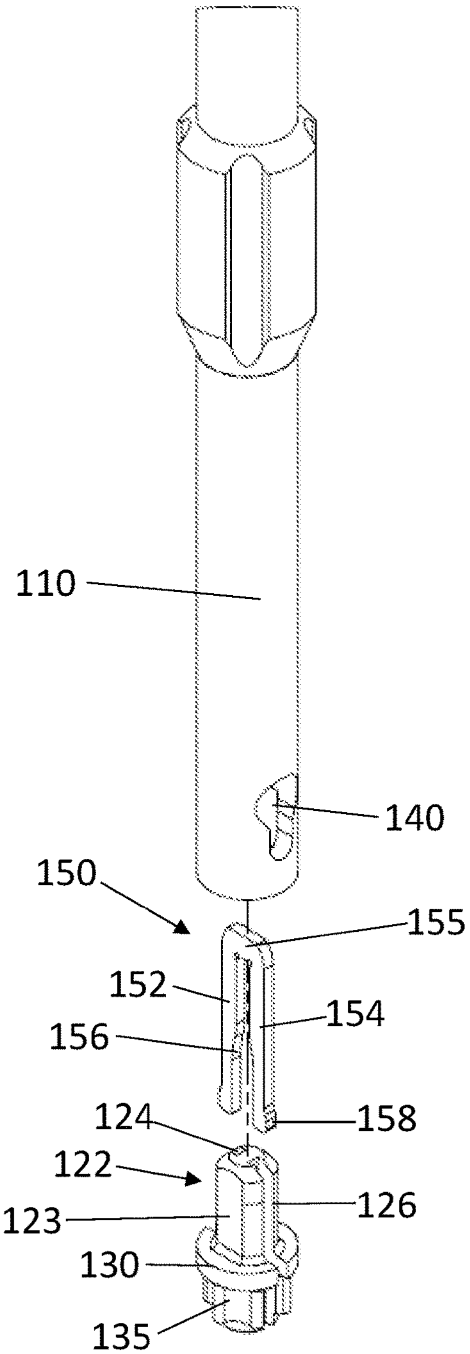
FIG. 5 is a close-up view of the distal portion D of FIG. 4.

An exploded view of retaining driver 100 is shown in FIG. 4, along with a close-up view of a distal portion D (or 120) shown in FIG. 5. Beginning with proximal end 102, handle 105 is threadably coupled to drive shaft 110, and thus is easily removable for replacement by an alternative gripping piece, a powered hand tool, robot arm or the like. Any means for detachably coupling handle 105 (or any other of the above-noted elements) to drive shaft 110 is contemplated, such as a quick connect or a spring-loaded protrusion on the drive shaft engaging with an aperture on the handle. Drive shaft 110 extends distally from handle 105, and a distal end of the drive shaft 110 is hollow defining a cavity for receiving portions of compressible winged member 150 and engaging tip 122 in the assembled configuration. An aperture 140 is defined in the surface of drive shaft 110 near the distal end of the drive shaft 110, and although only one aperture is illustrated, the drive shaft includes a second substantially similar aperture opposite the first aperture. The apertures provide clearance for compressible winged member 150 to compress and expand. Compressible winged member 150 defines a width spanning from an outer surface of a first wing 152 to an opposing outer surface of a second wing 154, and the width of compressible winged member 150 may taper as it extends distally. That is, compressible winged member 150 has a greater width at its proximal end, which generally aligns with apertures 140 and may protrude into and/or through the apertures. As compressible winged member 150 extends distally, the width tapers and compressible winged member 150 fits within the diameter of drive shaft 110.

As shown in FIG. 5, compressible winged member 150 includes first wing 152 and second wing 154 extending distally from a connecting base 155. Connecting base 155 extends in a direction perpendicular to the first and second wings 152, 154 and longitudinal axis X to connect the first and second wings which extend parallel to axis X, forming compressible winged member 150 as a single monolithic piece. First and second wings 152, 154 are generally parallel and mirror images of each other such that compressible winged member 150 is symmetric. As shown on first wing 152, each wing has an inner tapered surface 156 which faces radially inward (i.e., toward the opposing wing). Each wing 152, 154 has a width defined across the wing in the same direction which the connecting base 155 extends (i.e., perpendicular to the proximal-distal direction), and the width of each wing tapers along inner tapered surface 156 as the wing extends distally. A distal flared portion 158 is included at the distal end of each wing 152, 154 in which the width of each wing increases and the wings flare radially outwardly. Each flared portion 158 has a distal surface, and a radially outer portion of the distal surface may be tapered or beveled as shown in FIG. 3.

As noted above, engaging tip 122 includes proximal stem 123 extending proximally from circular base 130. Proximal stem 123 is generally circular (and includes beveled and/or flattened outer surfaces to ensure proper orientation of the tip with respect to the shaft) and is positioned within the cavity at the distal end of drive shaft 110 when retaining driver 100 is in the assembled configuration. Each component of engaging tip (e.g., proximal stem 123, circular base 130, corrugated portion 135 and distal head 128) has a recess along its radially outer surface aligned and in communication with the recess of the adjacent component(s) of engaging tip 122 forming a first slot 124 extending longitudinally along engaging tip 122. First slot 124 is sized and shaped to receive first wing 152 of compressible winged member 150 in the assembled configuration, and the depth of the first slot varies along its length to correspond to the width of first wing 152. Engaging tip 122 includes second slot 126 substantially similar to and located opposite first slot 124, the second slot sized and shaped to receive second wing 154 in substantially the same manner as first slot 124 and first wing 152.

Figure 6:
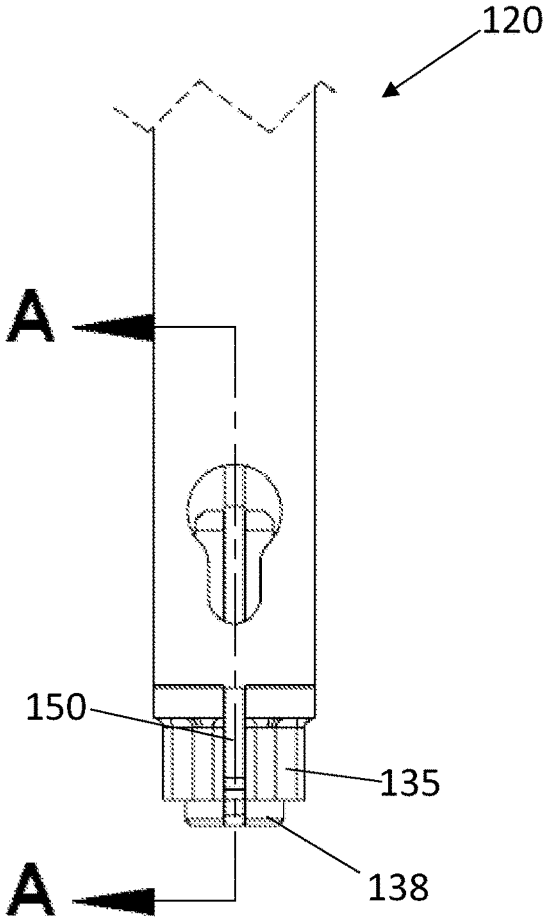
FIG. 6 is a side view of the distal portion of the retaining driver of FIG. 1.
Figure 7:
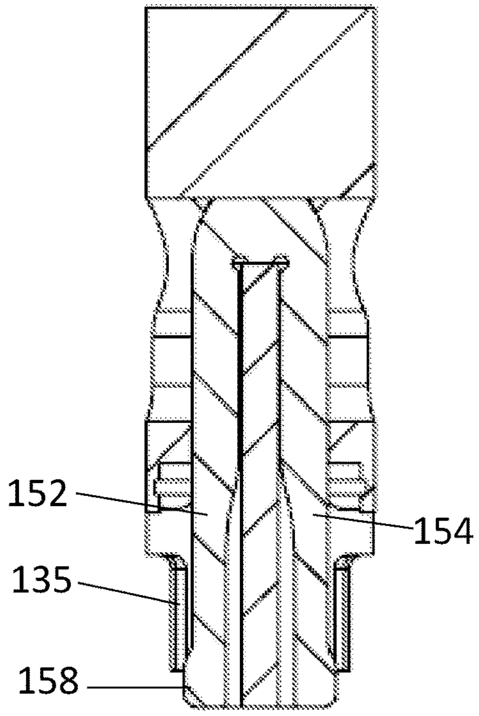
FIG. 7 is a cross-sectional view taken along the line A-A in FIG. 6.

A distal portion 120 and a cross-section of the distal portion of retaining driver 100 are shown in FIGS. 6 and 7, respectively, in the assembled configuration. As noted above, extending distally from corrugated portion 135 is distal head 138, which is generally circular and has two opposing recesses extending radially inward from the circumference and aligned with the recesses of corrugated portion 135, circular base 130 and proximal stem 123, to form slots 124 and 126 for receiving compressible winged member 150. The recesses of distal head 138 are separated by a center portion 139, as shown in FIG. 3, and are sized and shaped to receive the distal flared portion 158 of first and second wings 152, 154 in the assembled configuration. Corrugated portion 135 has an outer diameter measured from an outer surface of a first ridge 132 to an outer surface of an opposing ridge 132, and distal head 138 has a diameter smaller than the outer diameter of corrugated portion 135.

In the illustrated example, first and second wings 152, 154 are configured such that when the wings 152, 154 are positioned within their respective slots 124, 126 in the assembled configuration, an outer surface of each wing is located radially inward of an outer surface of engaging tip 122, with the exception of flared portions 158 extending beyond the circumference of distal head 138 as shown in FIG. 3. In other words, first and second wings 152, 154 do not protrude beyond the outer limits of corrugated portion 135 and circular base 130 to avoid interference of the wings with the set screw receiving portion that corresponds with corrugated portion 135. In other examples, the outer surface of each wing may protrude radially beyond the outer surface of the engaging tip for at least a portion of or for the entire length of the compressible winged member.

At rest, flared portions 158 of first and second wings 152, 154 are positioned partially inward and partially outward of the circumference of distal head 138, and a gap of space exists between each flared portion 158 and center portion 139, allowing the flared portions 158 to be compressed radially inwardly. Compressible winged member 150 may be formed of a material having a stiffness that causes a biasing force in first and second wings 152, 154 upon deflection to return to their resting states, but the wings are sufficiently flexible to be compressed radially inward. Flared portions 158 are approximately the same size as the recesses in distal head 138 that form slots 124, 126, so that when first and second wings 152, 154 are compressed radially inward, the flared portions fit within the recesses with inner surfaces abutting center portion 139 and outer surfaces generally aligning with the circumference of distal head 138. Alternatively, flared portions 158 may be smaller than the recesses in distal head 138, such that they may not abut center portion 139 when compressed radially inward, but their outer surfaces may still generally align with the circumference of distal head 138. Compressible winged member 150 may have any structure such that the first and second wings 152, 154 may be deformed from a resting state, and a biasing force encourages the wings to return to the resting state. For example, each wing may be pivotable about a hinge, and a spring may extend between first wing 152 and second wing 154 that may apply a biasing force in the radially outward direction when at least one of the first and second wings is compressed in the radially inward direction.

Figure 8:
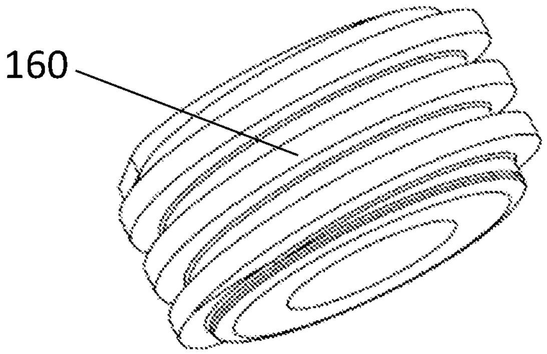
FIG. 8 is a perspective view of a set screw according to an embodiment of the disclosure.
Figure 9:
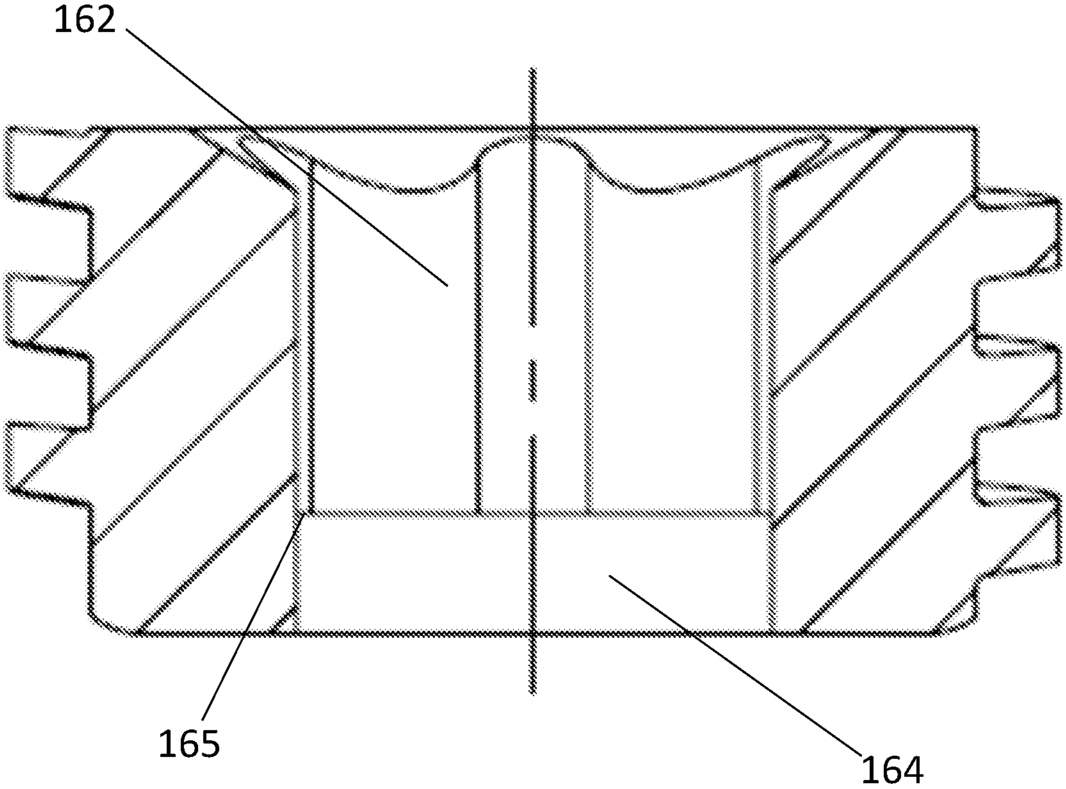
FIG. 9 is a cross-sectional view of the set screw of FIG. 8.
Figure 10:
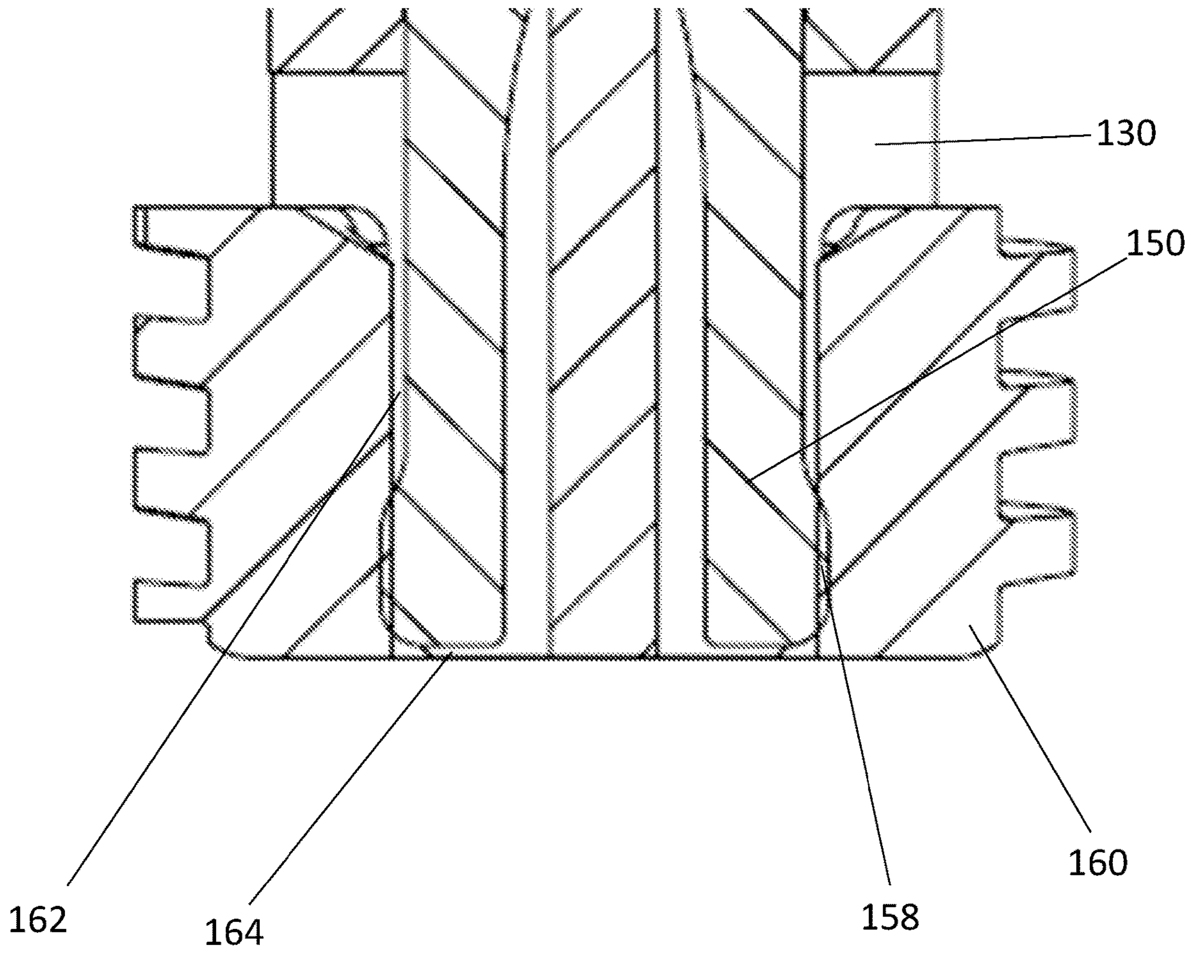
FIG. 10 is a cross-sectional view of the retaining driver of FIG. 1 engaged with the set screw of FIG. 8.

Retaining driver 100 may be used to mate with a set screw 160 as shown in FIGS. 8 and 9. Set screw 160 includes a proximal receiving portion 162 sized and shaped to receive corrugated portion 135 of engaging tip 122 to rotationally fix retaining driver 100 to set screw 160 when engaging tip 135 is inserted therein. Set screw 160 further includes a distal receiving portion 164 which is generally circular, sized and shaped to receive distal head 138 of engaging tip 122. Distal receiving portion 164 of set screw 160 has a diameter approximately the same as (or slightly larger than) a diameter of distal head 138 of engaging tip 122, wherein the diameter of distal head 138 does not include the protrusion of first and second wings 152, 154. Thus, first and second wings 152, 154 at rest are biased to protrude beyond the circumference of distal head 138, and the wings may be radially compressed to fit within distal receiving portion 164 of set screw 160.

When the wings 152, 154 are in a resting configuration (i.e., an uncompressed position), the distance between the radially outer surface of first wing 152 and the radially outer surface of second wing 154 is greater than a diameter of the second receiving portion 164 of set screw 160. In the compressed configuration or position, however, (e.g., one or both wings 152, 154 is/are subject to a radially inward force as described above), the interior surfaces of each wing abuts center portion 139, and the outer surface of the wings aligns with the circumference of the distal head 138, such that the wings in combination with distal head 138 create a full continuous circle having a diameter substantially equal to, or slightly less than, that of distal receiving portion 164 of set screw 160. Thus, when the wings 152, 154 are engaged with set screw 160 in the compressed configuration, the wings apply a biasing force in the radially outward direction onto the surrounding receiving portion 164 of set screw 160, thereby increasing friction and strengthening engagement between compressible winged member 150 and set screw 160. In other words, set screw 160 can be held in registration with retaining driver 100 because of this relationship.

In a method of using retaining driver 100, the driver may be received by a surgeon in a fully assembled configuration, e.g., with the engaging tip 122 and compressible winged member 150 coupled to the drive shaft 110. The surgeon may then use the tool by engaging the receiving portions of set screw 160 with engaging tip 122 and compressible winged member 150. That is, a corresponding receiving portion (e.g., distal receiving portion 164) of set screw 160 may be engaged with first and second wings 152, 154 of the compressible winged member 150, and a corresponding receiving portion of the set screw 160 (e.g., proximal receiving portion 162) may be engaged with corrugated portion 135 of engaging tip 122.

As described above, compressible winged member 150 is illustrated in FIG. 3, for example, at rest, but may be compressed such that the first and/or second wings 152, 154 move with respect to each other and with respect to distal head 138. For example, when engaging tip 122 is inserted into set screw 160, the beveled surfaces 137 of first and second wings 152, 154, contact an interior ledge 165 of set screw 160. The interior ledge 165 is formed between proximal receiving portion 162 and distal receiving portion 164 by a change in diameter from one portion to the other (e.g., proximal receiving portion 162 having a first internal diameter, and distal receiving portion 164 having a second internal diameter smaller than the first). The user may apply pressure between the distal end of retaining driver 100 and set screw 160 (e.g., by pushing the retaining driver distally relative to the set screw), and the contact between beveled surfaces 137 of wings 152, 154 and internal ledge 165 of set screw 160 creates a compressive (i.e., radially inward) force on the wings, pushing the wings closer together until the inner surface of each wing contacts center portion 139 of distal head 138.

When wings 152, 154 are pushed toward each other in the compressed configuration, the wings, along with distal head 138, may be inserted into distal receiving portion 164 of set screw 160, forming a stable connection between the engaging tip 122 and set screw 160 which may hold the set screw 160 in engagement with the retaining driver 100 to be easily handled and implanted. Retaining driver 100 may be decoupled from set screw 160 by translating one of retaining driver 100 or set screw 160 relative to the other, but engagement between compressible winged member 150 and the set screw 160 increases the translational force required to overcome the friction fit and decouple the retaining driver 100 from the set screw 160. In contrast to set screws having only a single sized receiving portion through the full length of the set screw, the structure of set screw 160 and the manner in which retaining driver 100 engages the set screw as described herein mitigates the risk of engaging the set screw in an incorrect orientation, e.g., upside down. However, it is indeed contemplated that retaining driver 100 may engage with a set screw or any other fastener/tool having a single sized aperture extending therethrough. In such an example, the beveled surfaces 137 of first and second wings

152, 154 may contact an outer surface or ledge of the set screw surrounding the aperture as engaging tip 122 is inserted into the aperture, and the compressible winged member 150 may transition into the compressed position immediately upon insertion into the aperture, and the distal head 138 may be translated through any length of the aperture. In some examples, the entire set screw aperture may be corrugated, sized and shaped to receive corrugated portion 135 such that distal flared portions 158 contact and apply a force to the convex portions of the interior surface of the set screw (e.g., the walls adjacent the aperture), and the corrugated portion 135 of retaining driver 100 may subsequently be inserted following distal head 138 to fit within the corrugated aperture of the set screw and rotationally fix the driver to the set screw.

As noted above, the interior surfaces of each wing need not contact center portion 139, so long as each wing is sufficiently compressed to fit within distal receiving portion 164 of set screw 160. It is contemplated that the wings 152, 154 may be formed such that they are not parallel to each other when compressible winged member 150 is at rest. In other words, wings 152, 154 may extend radially inwardly from connecting base 155 at rest to decrease the biasing force applied by flared portions 158, or the wings may extend radially outwardly from the connecting base 155 to increase the biasing force applied by the flared portions 158 when the retaining driver 100 is engaged with set screw 160.

When implanting a spinal rod into a patient, the spinal rod may be inserted into a plurality of coupling elements of pedicle screws anchored into the pedicles of the spine. The surgeon may thereafter use the driver 100 by pointing the distal end 104 into the coupling element to actuate a set screw over the spinal rod, thereby securing the spinal rod with the coupling element to create a stable fixation of the spinal rod to the spinal cord. The retaining driver 100 may then be completely disengaged from the set screw. It is contemplated that the structure described herein with respect to distal portion 120 may be incorporated on any other tool or device, such as a rod reducer used to implant a spinal rod into a patient. In other words, the structure of distal portion 120 of retaining driver 100 is not limited to application on a standalone tool, but may be applied as an element of other devices to create a multi-purpose device.

As noted above, any embodiments of the retaining driver described herein may be used in any context requiring a strong detachable engagement between the tool and another object, particularly a fastening device that requires rotation. For example, the retaining driver may be used in carpentry, construction, mechanical repairs, etc., with fasteners such as wood screws, metal screws, pins, bolts, nails, etc. shaped to mat with the engaging tip and compressible winged member of the retaining driver. The tool may also be used for the removal of the same or similar objects, particularly in too-far-to-reach locations, such as the ceiling of a room. For instance, engaging the tool with a fastener implanted in the ceiling may allow easy rotation of the fastener from the ground level and a steady grip with the fastener after it has been removed from its respective implant site to hold the fastener at the distal end of the tool and safely bring it down without the risk of it falling on the user.

In certain preferred embodiments, the components of the retaining driver may be formed of stainless steel. It is contemplated that any or all of the components of the retaining driver may be made of metals such as titanium, carbon steel, aluminum, or the like, or other spring materials used particularly for the compressible winged member such as nitinol. It is further contemplated that any or all of the components of the retaining driver may be formed of polymer materials such as plastics, polyethylene terephthalate (PET), polyether ether ketone (PEEK), or the like. Certain components may be formed from different materials than other components. For example, the drive shaft and/or the engaging tip may be formed from a different material than the compressible winged member. Any suitable length is contemplated for the retaining driver. In certain preferred embodiments, the compressible winged member may measure between approximately 0.25 and 0.75 inches in length, preferably about 0.5 inches, and may measure between approximately 0.125 and 0.25 inches in width, preferably about 0.15 inches. Corrugated portion 135 defines a minor diameter spanning from a radially innermost point of elongate rounded groove 134 to the same point of an opposing groove 134, and distal head 138 has a diameter equal to or less than the minor diameter of corrugated portion 135. In some examples, corrugated portion 135 may have a minor diameter of approximately 0.1566 inches, and distal head 138 may have any diameter equal to or less than 0.1566 inches, such as about 0.153 inches.

Figure 11:
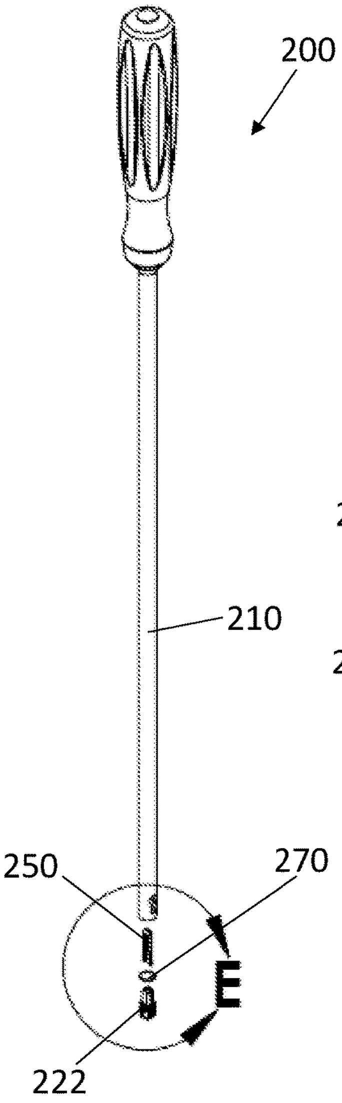
FIG. 11 is an exploded view of a retaining driver according to another embodiment of the disclosure.
Figure 12:
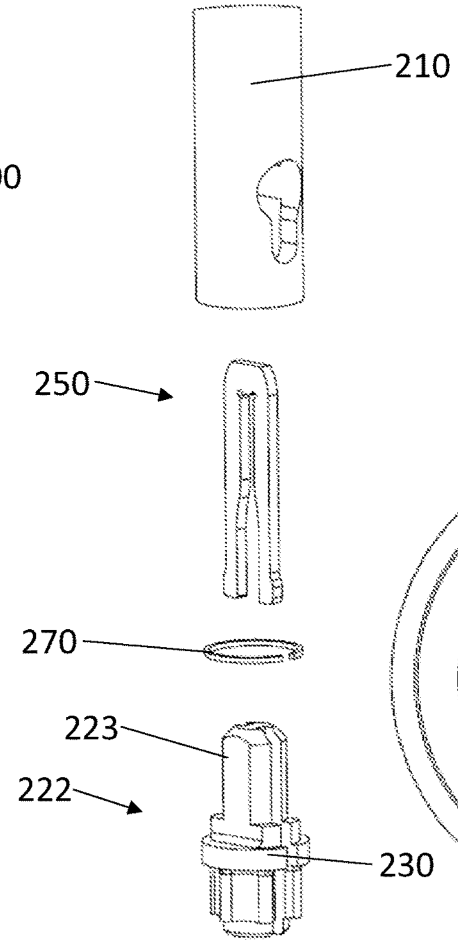
FIG. 12 is a close-up view of a distal portion E of FIG. 11.
Figure 13:
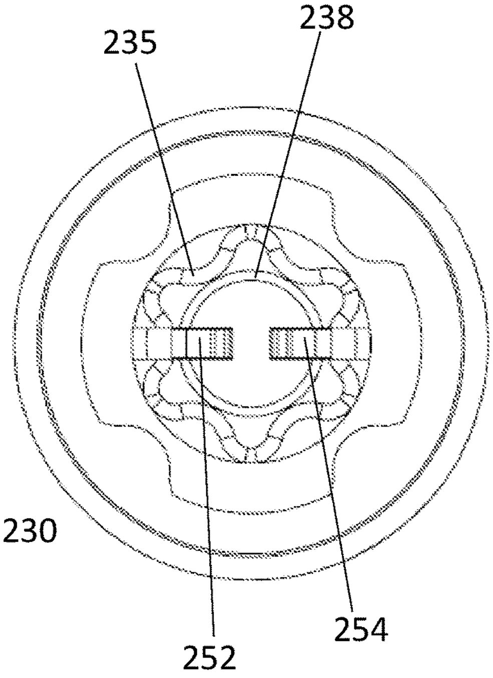
FIG. 13 is a distal view of the retaining driver of FIG. 11.

FIGS. 11-13 illustrate a retaining driver 200 according to another embodiment of the disclosure. Unless otherwise stated, like reference numerals refer to like elements of the above-described retaining driver 100, but within the 200-series of numbers. Retaining driver 200 is substantially similar to retaining driver 100, but includes the addition of retaining ring 270, which couples engaging tip 222 and drive shaft 210 with compressible winged member 250 sandwiched therebetween in the assembled configuration. Retaining ring 270 is positioned in an external groove (not shown) of engaging tip 222 (which may be located on proximal stem 223 or circular base 230) and a corresponding internal groove (not shown) of drive shaft 110, which is aligned with the groove of engaging tip 222 along the length of retaining driver 200 in the assembled configuration. Retaining ring 270 is sized and shaped such that it surrounds compressible winged member 250, but does not interact with nor interfere with compressible winged member 250 as it transitions between compressed and uncompressed positions while in use. FIG. 13 illustrates a distal view of retaining driver 200, showing the same components as retaining driver 100 to engage a fastener, such as distal head 238, corrugated portion 235, and first and second wings 252, 254 of compressible winged member 250.

The addition of retaining ring 270 allows engaging tip 222 and compressible winged member 250 to be decoupled from drive shaft 210 (as opposed to certain alternative embodiments, in which the engaging tip may be welded to the drive shaft), after which the same or a different engaging tip and compressible winged member may be reattached to the drive shaft. For example, after retaining driver 200 is used in a surgical operation, retaining driver 200 may be returned to the manufacturer or other maintenance provider to be properly cleaned and prepared for future operations, at which point engaging tip 222 and compressible winged member 250 may be decoupled from drive shaft 210 to thoroughly clean each piece, and thereafter recoupled or replaced with new respective pieces.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool for use with a fastener, the tool comprising:
a drive shaft extending along a longitudinal axis from a proximal end to a distal end;
an engaging tip extending from the distal end of the drive shaft, the engaging tip sized and shaped to detachably engage a receiving portion of the fastener, wherein the engaging tip is rotationally fixed to the fastener when the engaging tip is engaged with the fastener;
a compressible winged member extending distally from a cavity defined by the drive shaft, the compressible winged member moveable between compressed and uncompressed positions,
wherein a distal end of the compressible winged member is open-ended and configured to be compressed,
wherein the engaging tip includes a proximal stem positioned within the drive shaft, the proximal stem defining at least a portion of a slot adapted to receive the compressible winged member,
wherein the engaging tip includes a circular base coupled to a distal end of the proximal stem, the circular base defining at least a portion of the slot adapted to receive the compressible winged member,
wherein the engaging tip includes a corrugated portion extending distally from the circular base, the corrugated portion defining a plurality of ridges and grooves between each adjacent pair of ridges, and
wherein the corrugated portion defines at least a portion of the slot adapted to receive the compressible winged member.

2. The tool of claim 1, wherein the drive shaft has a distal portion adjacent the engaging tip, and wherein the cavity extends along the longitudinal axis and is configured to receive a portion of the compressible winged member.

3. The tool of claim 1, wherein the compressible winged member includes a first wing and a second wing connected by a connecting base.

4. The tool of claim 1, wherein the engaging tip includes a distal head extending distally from the corrugated portion and defining a circumference, the distal head defining at least a portion of the slot adapted to receive the compressible winged member.

5. The tool of claim 4, wherein the compressible winged member includes a first wing protruding radially beyond the circumference of the distal head when in a resting configuration, defining a first gap between the first compressible wing and a center portion of the distal head.

6. The tool of claim 5, wherein the first wing is biased in the uncompressed position and is configured to be compressed radially inward to close the first gap and have an outer edge of the first wing align with the circumference of the distal head when in the compressed position.

7. The tool of claim 6, wherein the compressible winged member includes a second wing protruding radially beyond the circumference of the distal head when in the uncompressed position, defining a second gap between the second wing and the center portion of the distal head.

8. The tool of claim 7, wherein the second wing is biased in the uncompressed position and is configured to be compressed radially inward to close the second gap and have an outer edge of the second wing align with the circumference of the head when in a compressed position.

9. The tool of claim 1, wherein the compressible winged member is disposed within a slot of the engaging tip.

10. The tool of claim 1, wherein the compressible winged member includes a first wing disposed within a first slot of the engaging tip and a second wing disposed within a second slot of the engaging tip.

11. A method of using a tool for use with a fastener, comprising:
inserting an engaging tip and a compressible winged member of the tool into a receiving portion of the fastener and contacting a distal surface of the compressible winged member to an internal ledge of the fastener to compress the compressible winged member radially inward within the receiving portion, the distal surface being farther from a user than a proximal end,
wherein the engaging tip includes a proximal stem positioned within a drive shaft, the proximal stem defining at least a portion of a slot adapted to receive the compressible winged member,
wherein the engaging tip includes a circular base coupled to a distal end of the proximal stem, the circular base defining at least a portion of the slot adapted to receive the compressible winged member,
wherein the engaging tip includes a corrugated portion extending distally from the circular base, the corrugated portion defining a plurality of ridges and grooves between each adjacent pair of ridges, and
wherein the corrugated portion defines at least a portion of the slot adapted to receive the compressible winged member; and
rotating the tool to rotate the fastener.

12. The method of claim 11, further comprising removing the compressible winged member and the engaging tip of the tool from the fastener by applying a force to the tool in a proximal direction relative to the fastener.

13. The method of claim 12, wherein the force applied is greater than a frictional force between the compressible winged member and the fastener.

14. The method of claim 11, further comprising removing the compressible winged member and the engaging tip of the tool from the fastener by applying a force to the fastener in a distal direction relative to the tool.

15. The method of claim 11, wherein the inserting step includes pressing a first distal beveled surface of a first wing and a second distal beveled surface of a second wing against the fastener.

* * * * *